(12) United States Patent
Pleszowski (10) Patent No.: US 9,248,039 B2
(45) Date of Patent: Feb. 2, 2016

(54) HEMORRHOID PAIN RELIEVING APPARATUS AND METHOD

(71) Applicant: Sergio Adrian Pleszowski, Montevideo (UY)

(72) Inventor: Sergio Adrian Pleszowski, Montevideo (UY)

( * ) Notice: Subject to any disclaimer, the term of this patent is extended or adjusted under 35 U.S.C. 154(b) by 0 days.

(21) Appl. No.: 14/047,429

(22) Filed: Oct. 7, 2013

(65) Prior Publication Data

US 2014/0034063 A1  Feb. 6, 2014

Related U.S. Application Data

(63) Continuation-in-part of application No. 13/583,735, filed as application No. PCT/BR2010/000278 on Aug. 23, 2010, now abandoned.

(51) Int. Cl.
*A61G 13/12* (2006.01)
*A61F 5/00* (2006.01)

(52) U.S. Cl.
CPC .................. *A61F 5/0093* (2013.01)

(58) Field of Classification Search
USPC ............... 128/845, 878, 95.1, 103.1, 98.1; 606/197; 4/237
See application file for complete search history.

(56) References Cited

U.S. PATENT DOCUMENTS

2004/0187213 A1*  9/2004  Wang ............................. 5/618

* cited by examiner

*Primary Examiner* — Ophelia A Hawthorne
(74) *Attorney, Agent, or Firm* — The Concept Law Group, P.A.; Scott D. Smiley; Erin A. Martin (57) ABSTRACT

The present invention includes a padded substantially planar upper-body surface, having a first end and is pivotally coupled at a pivot point to a floor-base containing a padded substantially planar lower-body surface, and having a second end and is pivotally coupled at a pivot point to a padded substantially planar pelvic surface. The present invention also includes a method wherein hemorrhoidal pain is relieved when a user, face down, positions its abdominal/pelvic area on the substantially planar pelvic surface, its lower body extremities on the substantially planar lower-body surface, and its upper body extremities and head on the substantially planar upper-body surface.

6 Claims, 5 Drawing Sheets

HEMORRHOID PAIN RELIEVING APPARATUS AND METHOD

CROSS-REFERENCE TO RELATED APPLICATION

This application claims priority to U.S. Non-provisional patent application Ser. No. 13/583,735, filed Sep. 10, 2012, which is a 371 National Stage Entry of PCT/BR10/00278, filed Aug. 23, 2010, the entirety of which is incorporated by reference.

FIELD OF THE INVENTION

The present invention relates generally to an apparatus and method for the relief of pain caused by hemorrhoids, and more particularly relates to a bodily positioning device with adjustable surfaces of bodily support to provide instant relief for hemorrhoid pain.

BACKGROUND OF THE INVENTION

It is believed that symptomatic hemorrhoids affect at least 50% of the U.S. population during their lives and around 5% of the population at any given time. Both sexes experience approximately the same incidence of the condition with rates peaking between 25 and 65 years of age. Symptomatic hemorrhoids are more common in Caucasians and those of higher socioeconomic status. The exact cause of symptomatic hemorrhoids is unknown. Several factors are believed to play a role in causing symptomatic hemorrhoids including: irregular bowel habits (constipation or diarrhea), a lack of exercise, nutritional factors (low-fiber diets), increased intra-abdominal pressure (prolonged straining, an intra-abdominal mass, or pregnancy), genetics, an absence of valves within the hemorrhoidal veins, and aging.

On one hand, hemorrhoids are a part of normal human anatomy and are complex vascular structures in the anal canal which help with stool control. In their physiological state, they act as a blood cushion composed of blood filled channels and connective tissue. On the other hand, hemorrhoids may become pathological when they become swollen or inflamed. There are two types of hemorrhoids, internal and external. Internal hemorrhoids are usually present with painless rectal bleeding while external hemorrhoids, if swollen, may produce significant pain and swelling in the area of the anus. When hemorrhoids become enlarged, they often cause issues with hygiene and may produce irritation of the surrounding skin and itchiness around the anus.

At the present time, there are no non-surgical advances in the treatment of swollen hemorrhoids or for the reduction of sinusoidal pressure in the hemorrhoidal plexus. Contrary to common perception, the consumption of vascular drugs and medications does not relieve the physical symptoms associated with an enlarged hemorrhoid. This is because the hemorrhoid cushions present in the anal canal are composed of blood vessels called sinusoids, connective tissue, and smooth muscle called the hemorrhoidal plexus. Unlike veins or arteries, sinusoids do not have muscle tissue in their walls, and therefore vascular medication does not help in the reduction of swelling of the hemorrhoidal plexus.

Therefore, a need exists to overcome the problems with the prior art as discussed above.

SUMMARY OF THE INVENTION

The invention provides a hemorrhoid pain relieving apparatus and method that overcomes the hereinafore-mentioned disadvantages of the heretofore-known devices and methods of this general type.

With the foregoing and other objects in view, there is provided, in accordance with the invention, a hemorrhoid pain relieving apparatus having a first end and a second end, a substantially planar upper-body surface, and a first support structure fixedly attached to the substantially planar upper-body surface that supports and distances the substantially planar upper-body surface a first distance from a floor. The support structure is a continuous structure at the first end of the apparatus.

The apparatus further includes a substantially planar lower-body surface, and a second support structure fixedly attached to the substantially planar lower-body surface that supports and distances the substantially planar lower-body surface a second distance from the floor. The second support structure is a continuous structure at the first end of the apparatus. Finally, the apparatus includes a substantially planar pelvic surface and a third support structure fixedly attached to the substantially planar pelvic surface that supports and distances the substantially planar pelvic surface a third distance from the floor that is higher relative to the first and second distance from the floor. The support structure is also a continuous structure between the first end and the second end of the apparatus.

In accordance with another feature, an embodiment of the present invention includes a hemorrhoid pain relieving apparatus, wherein the upper-body surface is a continuous surface that extends from the floor to the substantially planar pelvic surface. The substantially planar pelvic surface is pivotally coupled to the substantially planar upper-body surface by a first pivot point. The substantially planar upper-body surface is pivotally coupled to a base by a second pivot point.

In accordance with a further feature of the present invention, the hemorrhoid pain relieving apparatus includes the substantially planar pelvic surface and the substantially planar upper-body surface that are pivotally flattened within themselves into the base. Similarly, the first support structure, the second support structure, and the third support structure demountably couples to the base.

In accordance with a further feature of the present invention, an objective of the present invention is to relieve hemorrhoidal pain when a user, facedown, positions his abdominal/pelvic area on the substantially planar pelvic surface, his lower body extremities on the substantially planar lower-body surface, and his upper body extremities and head on the substantially planar upper-body surface.

In accordance with a further feature of the present invention, the first support structure, the second support structure, and the third support structure are height adjustable, and the substantially planar pelvic surface, the substantially planar upper-body surface, and the substantially planar lower-body surface are removable.

In accordance with a further feature of the present invention, the apparatus for relief of hemorrhoid pain and swelling includes a padded substantially planar upper-body surface, having a first end that is pivotally coupled at a first pivot point to a floor-base containing a padded substantially planar lower-body surface. The apparatus also includes a second end that is pivotally coupled at a second pivot point to a padded substantially planar pelvic surface. The apparatus further includes a first support structure that is adjustably coupled to the padded substantially upper-body surface and that is pivotally coupled to the floor-base at a third pivot point. The apparatus further includes a second support structure that is adjustably coupled to the padded substantially planar pelvic surface and that is pivotally coupled to the floor-base at a fourth pivot point. The padded substantially planar pelvic surface is shaped to receive a user's abdominal and pelvic area.

In accordance with the present invention, a method for relief of hemorrhoid pain is provided. The method includes the steps of placing a user's upper body extremities and head on a substantially planar upper-body surface fixedly coupled to a first support structure at a first end. The first support structure is spaced at a first distance from a floor. The method continues with the steps of placing a user's lower body extremities on a substantially planar lower-body surface fixedly coupled to a second support structure at a second end. The second support structure is spaced at a second distance from the floor. The method continues with the step of placing a user's abdominal and pelvic area on a substantially planar pelvic surface fixedly coupled to a third support structure between the first and the second end, the third support structure spaced at a higher distance from the floor relative to the first distance from the floor and the second distance from the floor.

In accordance with another feature, an embodiment of the present invention includes an upper-body surface that is a continuous surface extending from the floor to the substantially planar pelvic surface. In this embodiment, the first support structure, the second support structure, and the third support structure are height adjustable. Furthermore, the substantially planar pelvic surface, the substantially planar upper-body surface, and the substantially planar lower-body surface could be removable.

In accordance with yet another feature, an embodiment of the present invention includes the substantially planar pelvic surface pivotally coupled to the substantially planar upper-body surface by a first pivot point, and the substantially planar upper-body surface pivotally coupled to a base by a second pivot point.

Although the invention is illustrated and described as embodied in a hemorrhoid pain relieving apparatus and method, it is not intended to be limited to the details shown because various modifications and structural changes may be made without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting, but rather to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

In this document, the term "demountably coupled" should be understood to mean not permanently fixed or attached.

BRIEF DESCRIPTION OF THE DRAWINGS

The accompanying figures, where like reference numerals refer to identical or functionally similar elements throughout the separate views and which with the detailed description below are incorporated in and form part of the specification, further illustrate various embodiments and explain various principles and advantages all under the present invention.

DETAILED DESCRIPTION

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient bodily positioning apparatus with bodily support surfaces that provide instant relief for hemorrhoid pain and swelling. Embodiments of the invention provide a foldable bodily positioning apparatus, with both fixed and adjustable levels of bodily support, to give a user instant relief for hemorrhoid pain. In addition, embodiments of the invention provide a method for the relief of hemorrhoidal swelling and the reduction of sinusoidal pressure in the hemorrhoidal plexus.

The present invention further provides a novel bodily positioning apparatus that allows adjustment to levels of support to different body parts in order to elevate the hemorrhoidal area to provide pain relief. The invention can be provided in many embodiments of varying complexity, from a unitary device with no moving parts to an assembly with adjustable levels of bodily support features that provide a plurality of bodily positions for the relief of hemorrhoidal area swelling and the reduction of sinusoidal pressure in the hemorrhoidal plexus.

Figures 1, 1A:
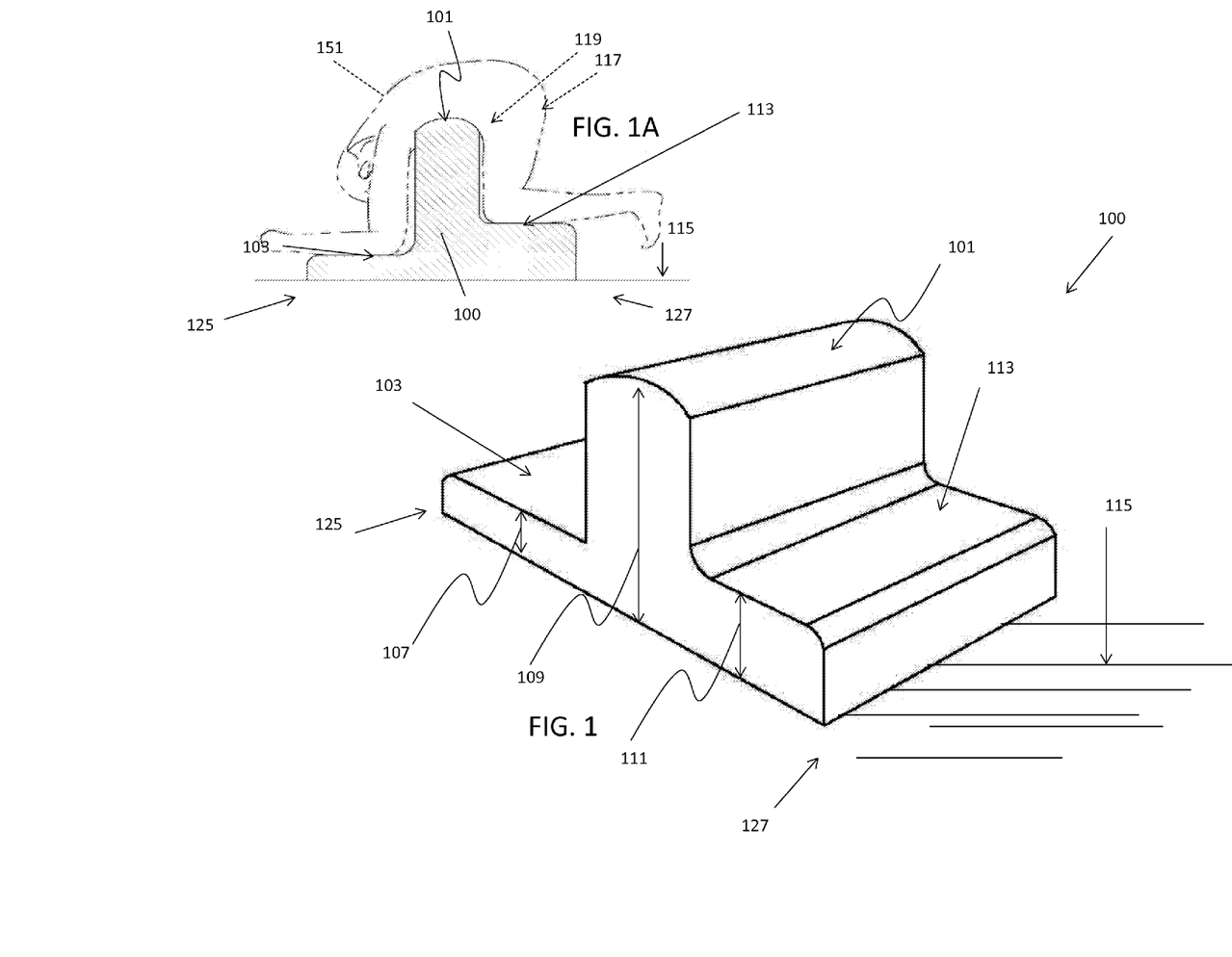
FIG. 1 is a downward-looking perspective view of a hemorrhoid pain relieving device that includes three supporting surfaces and three supporting structures in a unitary continuous form in accordance with the present invention.
FIG. 1A is an elevational side view showing the bodily positioning apparatus of FIG. 1 with a user in a kneeling position facedown on top of the bodily positioning apparatus.

Referring now to FIG. 1, one embodiment of the present invention is shown in a downward perspective view. FIG. 1 shows several advantageous features of the present invention, but, as will be described below, the invention can be provided in several shapes, sizes, combinations of features and components, and varying numbers and functions of the components. In this first embodiment of FIG. 1, the inventive bodily positioning apparatus 100 is a continuous unitary device that includes a first end 125 and a second end 127. Between the first end 125 and the second end 127 there are a three substantially planar surfaces, namely, a pelvic surface 101, an upper-body surface 103, and a lower-body surface 113.

On or about the middle of the bodily positioning apparatus 100, between the first end 125 and the second end 127, the substantially planar pelvic surface 101 is supported off of the floor 115 by a pelvic support structure 109. At the first end 125 of the bodily positioning apparatus 100, the substantially planar upper-body surface 103 is supported off of the floor 115 by an upper-body support structure 107. At the second end 127, located opposite the first end 125, the substantially planar lower-body surface 113 is supported off of the floor 115 by a lower-body support structure 111. It is envisioned that the distance from the floor 115 to the substantial planar support surfaces 101, 103, and 113 as shown in FIG. 1, may vary providing the pelvic surface 101 is at a higher distance and position relative to the upper-body surface 103, the lower-body surface 113, and the floor 115.

Referring now to FIG. 1A, a side view of the bodily positioning apparatus 100 of FIG. 1 is shown. It is intended that both FIG. 1 and FIG. 1A are viewed together. As shown in FIG. 1A, a user 151 is positioned facedown (facing the floor 115) so his head and arms are resting on the substantially planar upper-body surface 103 at the first end 125. In this position, the abdominal/pelvic section 119 of the user's body is resting on top of the substantially planar pelvic surface 101 in the middle of positioning apparatus 100. Simultaneously, at the second end 127, the user's knees and shins are comfortably resting on the lower-body surface 113. Here, the pelvic support structure 109 creates the highest distance from the floor 115 compared to upper-body support structure 107 and lower-body support structure 111. Therefore, the pelvic support structure 109 positions the substantially planar pelvic surface 101 higher in relation to both the upper-body surface 103 and the lower-body surface 113. As seen here, while the user 151 is facing the floor 115, his hemorrhoidal area 117 is in an elevated position, near or parallel to the pelvic surface 101. When a user 151 is conforming to the bodily positioning apparatus 100, it allows the hemorrhoidal area 117, the middle rear section of the body, to rest at the highest distance from the floor 115 and the rest of the body (usually a distance above the heart plane); hence, blood from the hemorrhoidal area 117 is moved down to the head and the upper and lower extremities due to the gravitational pull on the blood. Since the hemorrhoidal plexus is filled with blood, pain is relieved when gravity acts downward on the blood, thereby evacuating the hemorrhoidal area and diminishing inflammation.

The bodily positioning apparatus 100 of FIG. 1 is a continuous unitary device, meaning it does not include structural segments, and can be formed or cut out of a single piece of material. It is envisioned that the bodily positioning apparatus 100 could be manufactured so the support structures 107, 109, and 111 are at different heights to accommodate different body types, for example, men vs. women. It is further envisioned that the material used to create the bodily positioning apparatus 100 may include foams, Styrofoam, plastic, wood or any other similar material that can be formed in a unitary way according to FIG. 1.

Although the pelvic surface 101 is described as being substantially "planar," that term, as used herein, is not intended to indicate an entire lack of curvature or surface features. In at least one embodiment, the pelvic surface 101 is padded for comfort and has a slight curvature in all directions from a centerline extending along the pelvic surface 101. Comfort is advantageous because one use of the device, as shown in FIG. 1A, is with a user 151 lying on the pelvic surface 101. Therefore, a general definition of the term "substantially planar" is a general flat surface suitable for a human to lie facedown thereon, as shown in FIG. 1A. It is envisioned that the padding used includes foams, or foam combinations, wherein the foams are covered with leather (or synthetic leather), polyesters, or other similar cloth-type material and more.

Figure 2:
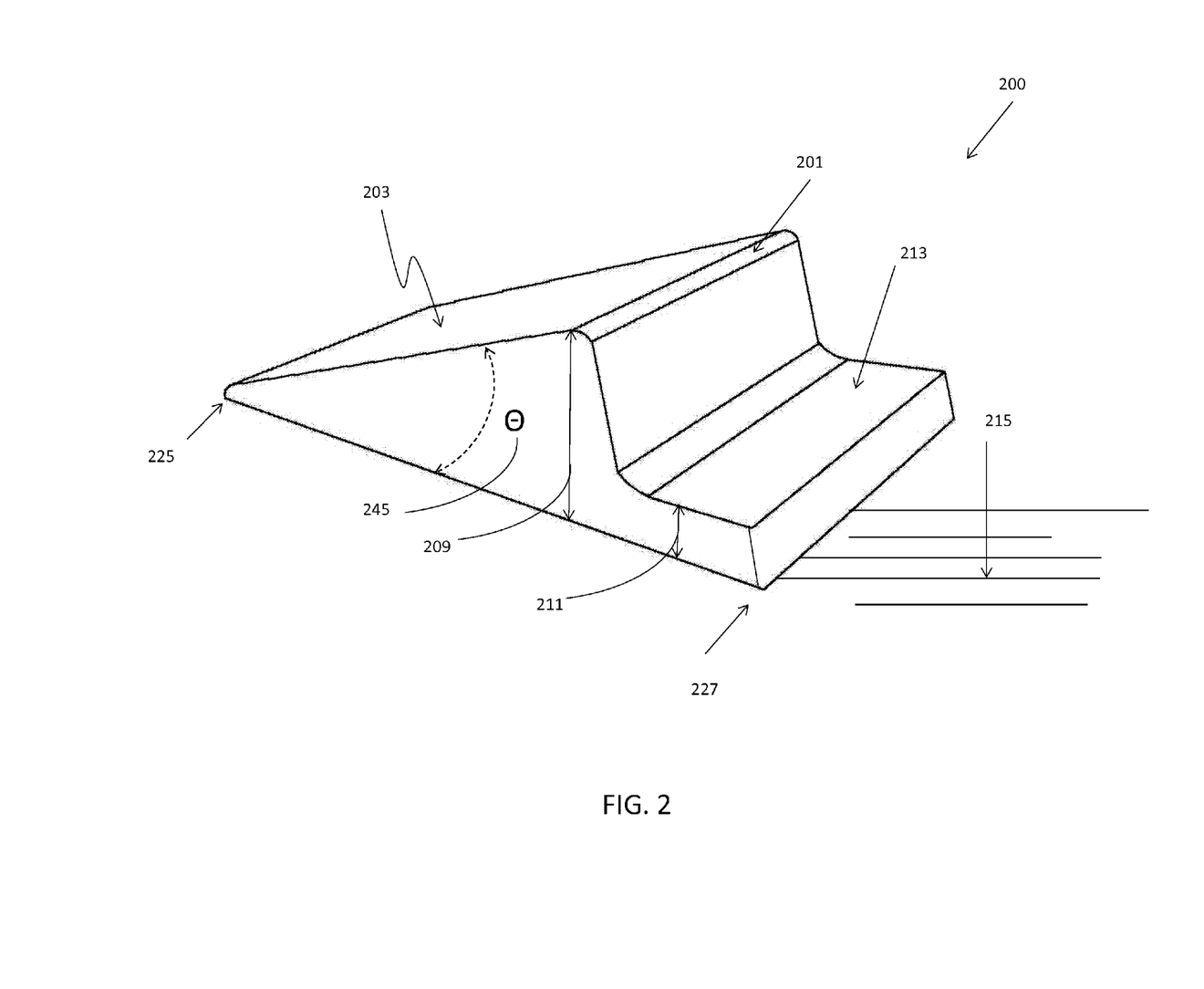
FIG. 2 is a downward-looking perspective view of an embodiment of the hemorrhoid pain relieving device that includes a first supporting surface that extends continuously from the floor to a second supporting surface and a third supporting surface elevated from the floor in a unitary continuous form.

FIG. 2 shows a downward-looking perspective view of another embodiment of the present invention. In this second embodiment, a body positioning apparatus 200 is a continuous unitary device, similar to the apparatus 100 in FIG. 1. The body positioning apparatus 200 has a first end 225 and a second end 227. Between the first end 225 and the second end 227 there is a substantially planar pelvic surface 201 supported off of the floor 215 by a pelvic support structure 209. At the first end 225, there is a substantially planar upper-body surface 203 that extends continuously from the floor 215 to the pelvic surface 201. Opposite the first end 225, on the second end 227, there is a substantially planar lower-body surface 213 supported off of the floor 215 by a lower-body support structure 211 at a shorter distance from the floor 215 than the pelvic surface 201. It is intended for a user (not shown) to lay in a kneeling-prone position facedown, placing his pelvic area on the pelvic surface 201, his head and arms on the upper-body surface 203, and his knees and shins on the lower-body surface 213. As it is shown in FIG. 2, the upper-body surface 203 is angled at a 45-degree angle 245 in relation to the floor 215. It is envisioned that the angle 245 between the upper-body surface 203 and the floor 215 may vary between approximately 0 degrees to 90 degrees where the upper-body surface 203 folds into the pelvic surface 201 to form a flat table (not shown).

Similar to the bodily positioning apparatus 100 in FIG. 1, here, in the bodily positioning apparatus 200 of FIG. 2, one of the intentions is to place the hemorrhoidal/anus area (the middle rear section of the human body) of a user to rest at the highest distance (here, the height of the pelvic support structure 209) from the floor 215, and the upper and lower body extremities near the floor 215. By placing the swollen hemorrhoidal area (shown previously in FIG. 1) at the highest position in the apparatus 200, and allowing the head, arms and legs at a lower position, blood from the vessels in the hemorrhoidal plexus will vacate. Hence, when the blood in the hemorrhoidal plexus is drained downward by gravitational force, immediate relief from pain in the swollen hemorrhoidal area is accomplished.

Figure 3:
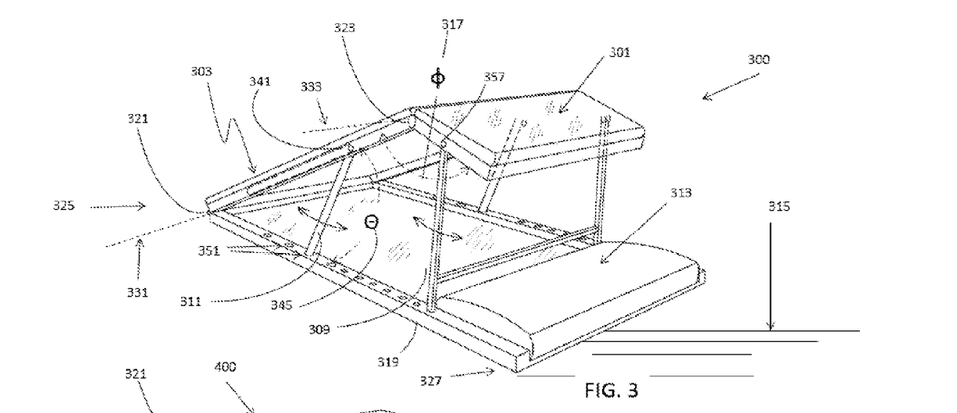
FIG. 3 is a downward-looking perspective view of a foldable hemorrhoid pain-relieving device that includes two adjustable supporting surfaces that are pivotally attached to each other by pivot points.

For ease of storage and transportation, according to an alternative embodiment of the present invention, and referring now to FIG. 3, a downward perspective view of a foldable bodily positioning apparatus 300 composed of structural segments is shown. Making the bodily positioning apparatus 300 foldable or transformable into a compacted version (shown as FIG. 4) is very convenient. It is intended for the bodily positioning apparatus 300 to be placed on the floor 315, usually in a bathroom or private room where it can be easily stored in a closet or underneath a bed. One of the benefits to this foldable version in FIGS. 3-4 is that it can be hidden from view, and when friends and visitors go to a user's bathroom, they will not wonder or question what the bodily positioning apparatus 300 is, hence avoiding embarrassment and uncomfortable explanations.

Figure 4:
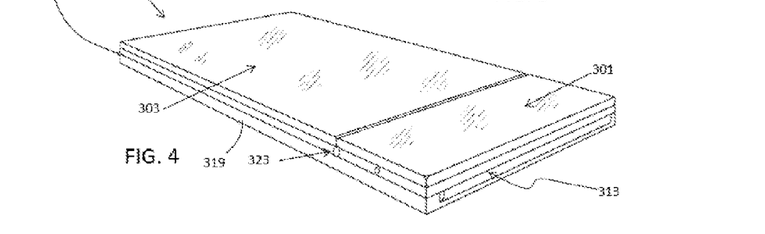
FIG. 4 is a downward-looking perspective view of the foldable hemorrhoid pain relieving device of FIG. 3 after it has been folded and flattened for easy storage.

Unlike the continuous unitary form of positioning apparatus 100 and 200 in FIG. 1 and FIG. 2, with reference now to FIG. 3 the structural segments or surfaces 301, 303, and 313 are separate but linked with a first pivot point 321 and a second pivot point 323 to convert the bodily positioning apparatus 300 into a foldable apparatus 400 shown in FIG. 4. It is envisioned that the first pivot point 321 and the second pivot point 323 are hinges or ratcheted hinges that pivot along their axis of rotation 331, 333 respectively, and can be locked in place at a specific angle such as 345 and 317 respectively. The foldable body positioning apparatus 300 includes a first end 325 and a second end 327. At the second end 327, the lower-body surface 313 is fixed to a floor-frame 319 that rests on a floor 315. Opposite the second end 327, at the first end 325, there is a substantially planar upper-body surface 303 that is pivotally linked to the floor-frame 319 by the first pivot point 321. The substantially planar upper-body surface 303 stretches from the first pivot point 321, located at or near the floor 315, to the pelvic surface 301 joined by the second pivot point 323. The substantially planar upper-body surface 303 is supported a distance from the floor 315 by upper-body support structure 311. The upper-body support structure 311 rotates around third pivot point 341 and locks into several female grooves 351 in the floor-frame 319. The female grooves 351 are designed to increase and decrease the distance between the upper-body surface 303 and the floor 315 about multiple angles 345 of rotation.

Similarly, the pelvic surface 301 is joined to the substantially planar upper-body surface 303 at the second pivot point 323. The pelvic surface 301 pivots at the location of the second pivot point 323 to increase and decrease the angle 317 between the pelvic surface 301 and the substantially planar upper-body surface 303. The pelvic surface 301 is supported by pelvic support structure 309 which locks into female grooves 351 on the floor-frame 319. The pelvic support structure 309 increases and decreases the distance between the pelvic surface 301 and the floor 315 by rotating about a fourth pivot point 357. Adjusting and rotating both the pelvic support structure 309 and the upper-body support structure 311 using pivots 341, 357 respectively, the user can best accommodate his/her body so that when placing the swollen hemorrhoidal area (shown previously in FIG. 1A) on the pelvic surface 301, his/her knees and shins are comfortably resting on the lower-body surface 313. This position will allow blood from the vessels in the hemorrhoidal plexus to vacate down to the extremities, thereby reducing pain and inflammation.

Similarly, it is envisioned that the upper-body surface 303 and the pelvic surface 301 can be adjustable by using the first pivot point 321 and the second pivot point 323, respectively. The upper-body support structure 311 creates different angles 345 to elevate or lower the pelvic surface 301. Advantageously, the adjustable upper-body support structure 311 accommodates users of different body shapes and heights. The pelvic surface 301 is sized and shaped to receive the user's abdomen or pelvic area, the upper-body surface 303 is sized and shaped to receive the user's head and arms, and the lower-body surface 313 is sized and shaped to receive the user's legs.

With reference now to FIGS. 3 and 4, another reason for the upper-body support structure 311 and pelvic support structure 309 to be adjustable is to create a foldable bodily positioning apparatus, such as the foldable bodily positioning apparatus 400 in FIG. 4. The foldable position of the bodily positioning apparatus 400 was created by using the first pivot point 321 and the second pivot point 323 to pivot the upper-body surface 303, and the pelvic surface 301, flat into the lower-body surface 313 and floor-frame 319. Advantageously, the low profile foldable bodily positioning apparatus 400 will fit into a closet, underneath a bed or behind a cabinet, giving the user convenient storage options.

Figure 5:
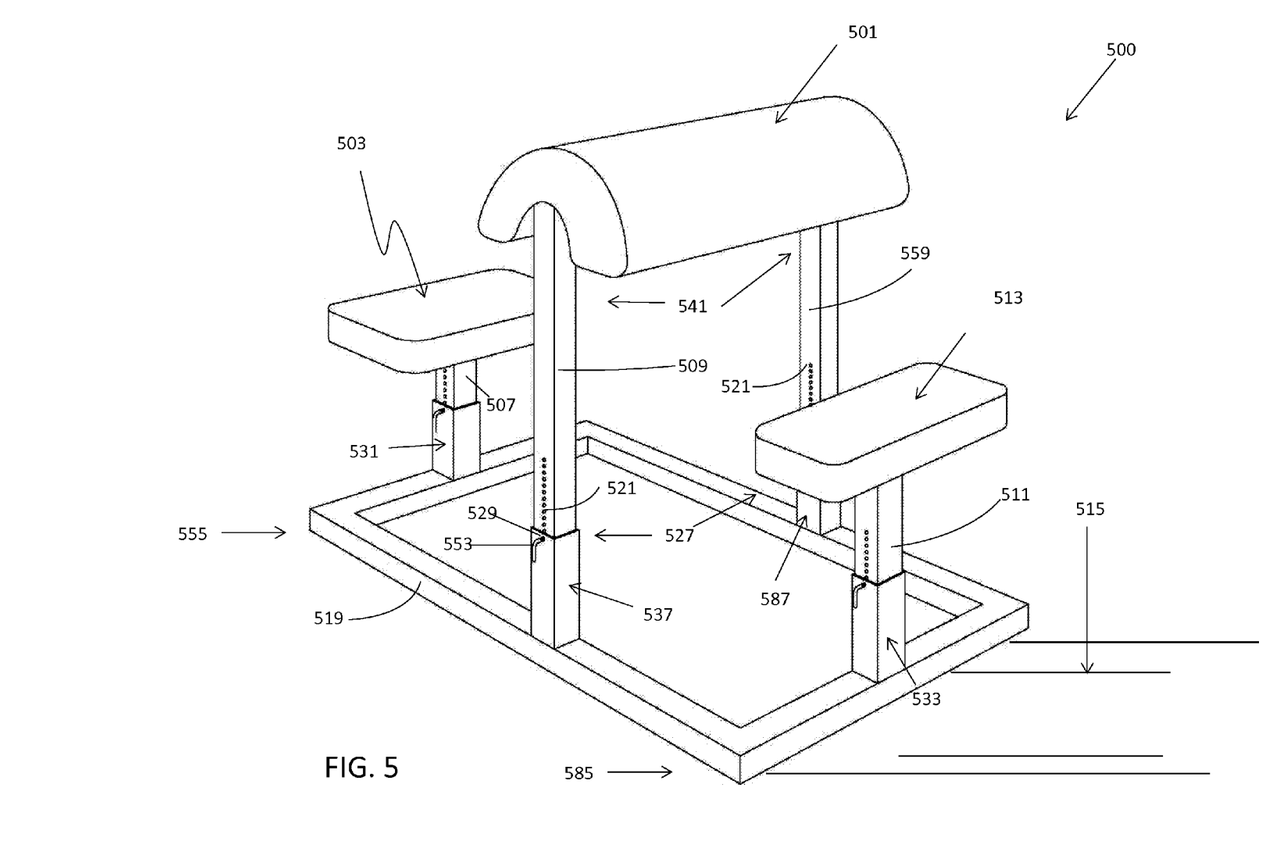
FIG. 5 is a downward-looking perspective view of a hemorrhoid pain-relieving device with up/down adjustable and removable supporting structures in accordance with an exemplary embodiment of the present invention.

FIG. 5 shows an additional embodiment of the bodily positioning apparatus 500, in a downward perspective view. Similar to the embodiments in FIGS. 1-3, FIG. 5 depicts the bodily positioning apparatus 500 having three support surfaces 501, 513, 503 located at different heights from each other and elevated from the floor 515 by four support structures 507, 509, 559, 511, placed on top of a floor-frame 519. Pelvic support surface 501 is located at a first end 555 of the bodily positioning apparatus 500, while the support surface 513 is located at a second end 585, opposite the first end 555. Similar to FIGS. 1-4, the pelvic support surface 501 is located between the first end 555 and the second end 585 of the bodily positioning apparatus 500. Here, the pelvic support surface 501 is supported by two support structures 509, 559, equally distanced from the floor 515. Floor-frame 519 includes female mounts 531, 537, 587, 533, that demountably couple with four support structures 507, 509, 559, 511, respectively. Advantageously, the support structures 507, 509, 559, 511, can be dismantled from the floor-frame 519 so that the bodily positioning apparatus 500 can be conveniently stored and hidden in compact places, such as a closet or underneath a bed. In one embodiment, wheels may be attached to the floor-frame 519 to easily transport the bodily positioning apparatus 500.

Referring still to FIG. 5, in one embodiment the pelvic surface 501 is supported at a maximum distance from the floor 515 by pelvic support structures 509, 559. The pelvic support structures 509, 559 each include two ends, a first end 541 fixedly attached to the pelvic surface 501, and a second end 527 demountably coupled to floor-frame 519 by female mounts 537, 587. The second end 527 defines a plurality of apertures 521 for a detent-pin 553 to be inserted through a matching aperture 529 in the female mounts 537, 587. The plurality of apertures 521 are spaced so each space adds or subtracts the distance from the pelvic surface 501 to the floor 515. One of the advantages of this embodiment is it allows for the pelvic support structure 509 to be raised and lowered to adjust to a user's body size.

Similar to pelvic support structure 509, the upper-body support structure 503 and the lower-support structure 511 may be raised and lowered by inserting detent-pins, such as detent-pin 553, through matching apertures, such as matching apertures 529, in female mounts 531, 533 respectively. Since the distance between the knees to the pelvic area varies from user to user, by adjusting the support structures 511, 503, the swollen hemorrhoidal area (FIG. 1) is designed to remain at the highest location in the apparatus 500. It is an objective of the present invention that, by allowing the head, arms, and legs to be placed at the lower location on top of support structures 511, 503, blood from the vessels in the hemorrhoidal plexus will vacate, and hence provide relief from pain.

Figure 6:
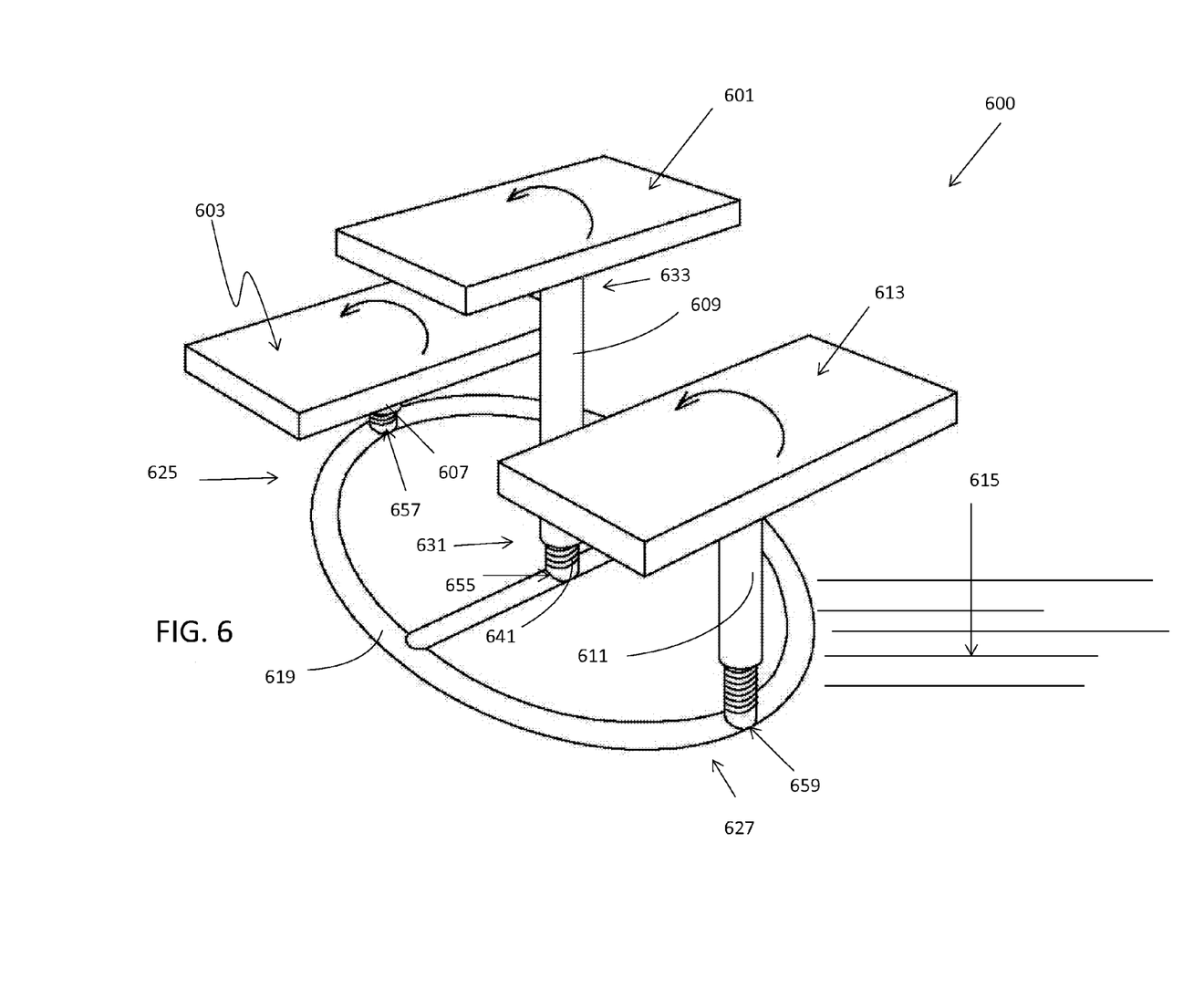
FIG. 6 is a downward-looking perspective view of a hemorrhoid pain-relieving device with rotationally adjustable and removable supporting structures in accordance with an exemplary embodiment of the present invention.

FIG. 6 provides a downward perspective view of another embodiment of the present invention. In this embodiment, the body positioning apparatus 600 is similarly structured to the bodily positioning apparatus 500 of FIG. 5. A base 619 can be separated or decoupled from support structures 609, 611, 607. Here, a pelvic surface 601 is supported at a maximum distance from the floor 615 by the pelvic support structure 609. The pelvic support structure 609 includes two ends, a first end 631 and a second end 633. The pelvic support structure 609 is fixedly attached to the pelvic surface 601 and the second end 633. The first end 631 is demountably pivotally coupled to the base 619 by a female internal thread (not shown) inside the pelvic support structure 609. The user may adjust the height of the pelvic surface 601 by turning it around and threading up or down the pelvic support structure 609 into the matching externally threaded male mount 655 fixed to the base 619.

At the first end 625 of the body positioning apparatus 600, a user may adjust the height of the upper-body surface 603 by turning it around and threading up or down the upper-body support structure 607 into an internal female thread (not shown) into a matching externally threaded male mount 657 fixed to the base 619. Similarly, at the second end 627, opposite the first end 625, the user may adjust the height of the lower-body surface 613 by turning it around and threading up or down the lower-body support structure 611 into an internal female thread (not shown) into a matching externally threaded male mount 659 fixed to the base 619. One of the advantages of this embodiment allows for the bodily surfaces 601, 603, 613, to be raised and lowered to adjust to the user's body size. Different heights of the bodily surfaces 601, 603, 613, allow for the bodily positioning apparatus 600 to be used by people of different body sizes to relieve the pain and inflammation concentrated in their hemorrhoidal plexus.

A bodily positioning apparatus has been disclosed using novel adjustable levels of support to different body parts to elevate the hemorrhoidal area to provide for pain relief in the hemorrhoidal plexus. The invention provides many embodiments, from a unitary device with no moving parts to a complex assembly with adjustable levels of bodily support features that provide a plurality of body positions for the relief of hemorrhoidal pain and the reduction of sinusoidal pressure of their hemorrhoidal plexus.

What is claimed is:

1. An apparatus for relief of hemorrhoid pain and swelling comprising:
    a padded substantially planar upper-body surface, having a first end directly coupled at a first pivot point to a floor-base containing a padded substantially planar lower-body surface, and having a second end directly coupled at a second pivot point to a padded substantially planar pelvic surface;
    a first support structure adjustably coupled to the padded substantially planar upper-body surface and directly coupled to the floor-base at a third pivot point; and
    a second support structure adjustably coupled to the padded substantially planar pelvic surface and directly coupled to the floor-base at a fourth pivot point.

2. The apparatus of claim 1, wherein:
    the padded substantially planar upper-body surface is a continuous surface that extends from a floor to the padded substantially planar pelvic surface.

3. The apparatus of claim 1, wherein:
    the padded substantially planar pelvic surface and the padded substantially planar upper-body surface are pivotally flattened within themselves into the floor-base.

4. The apparatus of claim 1, wherein:
    the first support structure and the second support structure demountably couple to the floor-base.

5. The apparatus of claim 1, wherein:
    the first support structure and the second support structure adjust a distance from the floor-base.

6. The apparatus of claim 1, wherein:
    the padded substantially planar pelvic surface, the padded substantially planar upper-body surface, and the padded substantially planar lower-body surface are removable.

\* \* \* \* \*